(12) United States Patent
Uber, III et al.

(10) Patent No.: US 9,814,827 B2
(45) Date of Patent: *Nov. 14, 2017

(54) SYSTEMS AND METHODS OF DELIVERING A DILATED SLURRY TO A PATIENT

(71) Applicant: BAYER HEALTHCARE LLC, Whippany, NJ (US)

(72) Inventors: Arthur E Uber, III, Pittsburgh, PA (US); David M Griffiths, Pittsburgh, PA (US); David M Reilly, Pittsburgh, PA (US); Alan D Hirschman, Glenshaw, PA (US); Kevin P Cowan, Allison Park, PA (US); Mark Trocki, Cheswick, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1121 days.

This patent is subject to a terminal disclaimer.

(21) Appl. No.: 13/772,849

(22) Filed: Feb. 21, 2013

(65) Prior Publication Data

US 2013/0172811 A1 Jul. 4, 2013

Related U.S. Application Data

(62) Division of application No. 11/960,968, filed on Dec. 20, 2007, now Pat. No. 8,382,704.

(Continued)

(51) Int. Cl.
*A61M 5/14* (2006.01)
*A61M 5/172* (2006.01)
(Continued)

(52) U.S. Cl.
CPC ........ *A61M 5/1407* (2013.01); *A61M 5/1723* (2013.01); *B01F 7/00258* (2013.01);
(Continued)

(58) Field of Classification Search
CPC .... A61J 1/20; A61M 25/0116; A61M 5/1452; A61M 5/14526; A61M 5/1454;
(Continued)

(56) References Cited

U.S. PATENT DOCUMENTS

| 1,572,075 A | 2/1926 | Painter |
| 3,370,754 A | 2/1968 | Cook et al. |

(Continued)

FOREIGN PATENT DOCUMENTS

| EP | 222718 | 11/1993 |
| EP | 0554352 | 5/2003 |

(Continued)

OTHER PUBLICATIONS

Dass, C.R., et al., "Microsphere-Mediated Targeted Gene Therapy of Solid Tumors", Drug Delivery, vol. 6, No. 4, Oct. 1, 1999, pp. 243-252(10).

(Continued)

*Primary Examiner* — Theodore Stigell
(74) *Attorney, Agent, or Firm* — Joseph L. Kent; David Schramm; James R. Stevenson

(57) ABSTRACT

A system for delivering to a patient a slurry which includes a fluid and a material that is non-dissolvable or immiscible in the fluid. The system includes a container adapted to contain the slurry and a supernate of the slurry, a syringe adapted to contain the slurry after dilation with the supermate, a fluid path between the syringe and the contents of the container, the fluid path including a needle at least partially disposed within the contents of the container, a plunger disposed in the syringe and adapted to create pressure in the syringe to cause a dilated slurry to flow into the syringe through the fluid path, and a fluidizing systen associated with the container and comprising a holder adapted to move (Continued)

the needle within the container to affect dilation of the slurry with a portion of the supernate.

22 Claims, 9 Drawing Sheets

Related U.S. Application Data

(60) Provisional application No. 60/877,777, filed on Dec. 29, 2006.

(51) Int. Cl.
| | |
|---|---|
| *B01F 7/00* | (2006.01) |
| *B01F 7/08* | (2006.01) |
| *B01F 9/10* | (2006.01) |
| *B01F 11/00* | (2006.01) |
| *B01F 11/02* | (2006.01) |
| *B01F 13/00* | (2006.01) |
| *B01F 13/08* | (2006.01) |
| *A61M 5/142* | (2006.01) |

(52) U.S. Cl.
CPC ...... *B01F 7/00566* (2013.01); *B01F 7/00908* (2013.01); *B01F 7/086* (2013.01); *B01F 9/103* (2013.01); *B01F 11/0071* (2013.01); *B01F 11/0074* (2013.01); *B01F 11/0082* (2013.01); *B01F 11/025* (2013.01); *B01F 13/002* (2013.01); *B01F 13/0023* (2013.01); *B01F 13/0818* (2013.01); *A61M 5/14216* (2013.01); *A61M 5/14236* (2013.01); *A61M 2202/09* (2013.01)

(58) Field of Classification Search
CPC ...... A61M 5/2066; A61M 2005/14533; A61M 5/1407; A61M 5/1723; C12M 1/26; C12M 1/268; C12M 1/28; C12M 1/32; C12M 1/3453; C12M 3/006; C12M 3/02; C12M 27/00; C12M 27/02; C12M 27/16; C12M 33/04; C12M 41/42; B01F 7/00258; B01F 7/00566; B01F 7/00908; B01F 7/086; B01F 9/103; B01F 11/0071; B01F 11/0074; B01F 11/0082; B01F 11/025; B01F 13/002; B01F 13/0023; B01F 13/0818
USPC .......................................................... 604/82
See application file for complete search history.

(56) References Cited

U.S. PATENT DOCUMENTS

| | | | |
|---|---|---|---|
| 3,373,906 A | 3/1968 | Hart et al. | |
| 3,477,432 A | 11/1969 | Shaw | |
| 3,601,372 A * | 8/1971 | Harmes | B01F 11/0014 137/579 |
| 3,606,094 A | 9/1971 | Mills et al. | |
| 3,831,903 A | 8/1974 | Harmel, Jr. | |
| 3,951,387 A | 4/1976 | Warden et al. | |
| 4,172,457 A | 10/1979 | Choksi et al. | |
| 4,543,094 A | 9/1985 | Barnwell | |
| 4,677,980 A | 7/1987 | Reilly et al. | |
| 4,704,105 A | 11/1987 | Adorjan et al. | |
| 4,808,184 A | 2/1989 | Tepic | |
| RE32,974 E | 7/1989 | Porat et al. | |
| 4,934,379 A | 6/1990 | Marzolf et al. | |
| 5,071,040 A | 12/1991 | Laptewicz, Jr. | |
| 5,120,135 A | 6/1992 | Ullman | |
| 5,176,446 A | 1/1993 | Chiba et al. | |
| 5,240,322 A | 8/1993 | Haber et al. | |
| 5,275,582 A | 1/1994 | Wimmer | |
| 5,290,228 A | 3/1994 | Uemura et al. | |
| 5,354,285 A | 10/1994 | Mazurik et al. | |
| 5,383,858 A | 1/1995 | Reilly et al. | |
| 5,385,564 A | 1/1995 | Slater et al. | |
| 5,425,580 A | 6/1995 | Beller | |
| 5,494,036 A | 2/1996 | Uber, III et al. | |
| 5,629,201 A * | 5/1997 | Nugteren | C12M 23/10 422/504 |
| 5,647,851 A * | 7/1997 | Pokras | A61M 5/20 604/131 |
| 5,660,796 A * | 8/1997 | Sheehy | G01N 35/1079 422/512 |
| 5,779,668 A | 7/1998 | Grabenkort | |
| 5,810,773 A | 9/1998 | Pesnicak | |
| 5,840,026 A | 11/1998 | Uber, III et al. | |
| 5,873,861 A | 2/1999 | Hitchins et al. | |
| 5,908,054 A | 6/1999 | Safabash et al. | |
| 6,048,551 A | 4/2000 | Hilfinger et al. | |
| 6,062,722 A | 5/2000 | Lake | |
| 6,385,483 B1 | 5/2002 | Uber, III et al. | |
| 6,410,334 B1 | 6/2002 | Schmolz | |
| 6,432,604 B1 | 8/2002 | Meyer et al. | |
| 6,575,930 B1 | 6/2003 | Trombley, III et al. | |
| 6,652,489 B2 | 11/2003 | Cowan et al. | |
| 6,699,214 B2 | 3/2004 | Gellman | |
| 6,706,020 B1 | 3/2004 | Urich | |
| 6,726,650 B2 | 4/2004 | Schneider et al. | |
| 6,758,828 B2 | 7/2004 | Hammer et al. | |
| 6,814,482 B2 | 11/2004 | Meyer et al. | |
| 6,939,302 B2 | 9/2005 | Griffiths et al. | |
| 6,970,735 B2 | 11/2005 | Uber, III et al. | |
| 7,244,248 B2 | 7/2007 | Azzolini | |
| 7,351,221 B2 | 4/2008 | Trombley, III et al. | |
| 7,713,232 B2 | 5/2010 | Uber, III et al. | |
| 8,382,704 B2 * | 2/2013 | Uber, III | B01F 7/00258 604/82 |
| 2001/0018571 A1 | 8/2001 | Hughes | |
| 2004/0092883 A1 | 5/2004 | Casey, II et al. | |
| 2004/0127846 A1 | 7/2004 | Dunn et al. | |
| 2005/0176140 A1* | 8/2005 | Benedict | C12M 23/58 435/366 |
| 2005/0287670 A1* | 12/2005 | Gulliver | C12M 27/02 435/455 |
| 2006/0037634 A1 | 2/2006 | Vorholz et al. | |
| 2006/0199260 A1* | 9/2006 | Zhang | B01F 13/0059 435/293.1 |
| 2007/0106208 A1 | 5/2007 | Uber, III et al. | |
| 2007/0244429 A1 | 10/2007 | Nguyen et al. | |

FOREIGN PATENT DOCUMENTS

| | | |
|---|---|---|
| FR | 2714833 | 7/1995 |
| GB | 2229374 A | 9/1990 |
| WO | 9927981 | 6/1999 |
| WO | 2007056247 | 5/2007 |

OTHER PUBLICATIONS

Hoshino, K., et al., "Three Catheter-based Strategies for Cardiac Delivery of Therapeutic Gelatin Microspheres", Gene Therapy (2006) 13, 1320-1327.
Wong, K. et al., "Overview of Microcarrier Culture, Cellular Bioprocess Technology", University of Minnesota, 1-8 (2004).
Abulnaga, B.E., "Slurry Systems Handbook", McGraw-Hill, (2002).
Wong, K. et al., "Overview of Microcarrier Culture", Cellular Bioprocess Technology, Univeristy of Minnesota, 1-8 (2004).
Dewitz, TS, Hung, TC, Russel, RM, McIntire, LV., "Mechanical Trauma in Leukocytes", Journal of Laboratory and Clinical Medicine, 90: 728-736 (1977).
Kameneva, M.V. et al., "Effects of Turbulent Stress upon Mechanical Hemolysis: Experimental and Computational Analysis", ASAIO Journal, 418-423 (2004).
Mardikar, S.H. and Niranjan, K., "Observations on the Shear Damage to Difference Animal Cells in a Concentric Cylinder Viscometer", Communications to the Editor, Biotechnology and Bioengineering, 68:6, 697-704 (2000).

(56) References Cited

OTHER PUBLICATIONS

Iveson, S.M. and Franks, G.V., "Particle Technology Demonstrations for the Classroom and Laboratory", Chemical Engineering Education, 274-280 (2003).
Subramanian, R.S., "Flow through Packed Beds and Fluidized Beds", Clarkson University, CH301: Fluid Mechanics, Fall 2003.
"Blood Cell Damage by Artificial Organ Devices is Focus of University of Pittsburgh Scientist's Talk at International Congress of Biorheology", UPMC New Bureau, Sep. 2002, 3 pgs.
Titan Pharmaceuticals, Inc., "Products and Technology: Spheramine", WayBackMachine, Nov. 2006, <http://web.archive.org/web/20061111043026/http://www.titanpharm.com/pt-spheramine.html>.
Blood Cell Damage by Artificial Organ Devices is Focus of University of Pittsburgh Scientists Talk at International Congress of Biorheology, News Bureau, University of Pittsburgh Medal Center (UPMC), 2002.1-3, presented at the 11th International Congress of Biorheology at Antalya, Turkey.
Spheramine, Titan Pharmaceuticals, Inc. (www.titanpharm.com/pt-spheramine.html), last visited Dec. 17, 2007.
U.S. Appl. No. 60/734,035, filed Nov. 4, 2005, Gelblum.
U.S. Appl. No. 60/742,224, filed Dec. 5, 2005, Gelblum.
U.S. Appl. No. 60/771,206, filed Feb. 7, 2006, Gelblum.

* cited by examiner

SYSTEMS AND METHODS OF DELIVERING A DILATED SLURRY TO A PATIENT

CROSS-REFERENCE TO RELATED APPLICATION

This application claims the benefit of U.S. patent application Ser. No. 11/960,968, filed on Dec. 20, 2007, now U.S. Pat. No. 8,382,704, which claims the benefit of U.S. Provisional Application No. 60/877,777, filed on Dec. 29, 2006, which are incorporated herein by reference.

BACKGROUND OF THE INVENTION

The present invention relates generally to devices, systems and methods of delivery of a slurry to a patient and, particularly, to devices, systems and methods of delivering a slurry including living cells to a patient.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosures of the references cited herein are incorporated by reference.

In a number of medical procedures, it is desirable to inject a multi-component injection medium into a patient. A multi-component injection medium is one that contains two or more effectively immiscible or insoluble materials or phases. (The term effective is used because they may ultimately dissolve or mix, but not in the time frame of interest for the imaging procedure.)

One example of such a medical procedure is ultrasound imaging, where small bubbles are contained or delivered in a liquid. The injection medium is injected into the veins, arteries, or tissue of the patient and provides increased ultrasound image signal or contrast. See, for example, U.S. Pat. No. 6,575,930.

A second example of delivery of a multi-component medium occurs in cell therapies in which cells in a carrier liquid are injected into the patient. The cells do not dissolve in the carrier liquid. Depending upon the disease or condition to be treated, the injection medium can be injected into arteries, tissue, or veins. A therapeutically effective fraction of the cells preferably remains intact and alive, and so constitute one material that is immiscible in the liquid or blood used for the liquid component of the injectate.

A third example of delivery of a multi-component medium is the delivery of cells on carrier beads or in or on a cell matrix of some kind. An example of such a medium is SPHERAMINE®, a treatment for Parkinson's disease being tested by Titan Pharmaceuticals, Inc. of San Francisco, Calif. SPHERAMINE is, for example, described in U.S. Patent Application Publication No. 2006/0037634. SPHERAMINE treatment involves implanting human retinal pigment epithelial cells on cell-carrying microcapsules or microspheres into the brain. Cell-carrying microcapsules and other microcapsules are described, for example, in EP 0554352 and EP 0222718. Such microcapsules can, for example, be made of glass, other silicon oxides, polystyrene, polypropylene, polyethylene, polyacrylamide, polycarbonate, polypentene, acrylonitrile polymers, nylon, amylases, collagen, polysaccharides, magnetite beads or formed of a gel or gelatin. The typical size of the microcapsules is approximately 10-500 microns. The cells are grown or implanted onto or into the microcapsules. The microcapsules can, for example, be implanted into sensitive tissue such as the brain to provide a medical treatment.

A fourth example of a multi-component medium includes small beads or spheres that can be used to embolize a tumor. The spheres are sufficiently large that they cannot pass through the smaller down stream vessels, but are sufficiently small that they can be carried along by a fluid through a catheter into the desired vessel. These spheres can optionally incorporate chemicals that provide pharmaceutical action, such as chemotherapy drugs for reducing (in size and/or number) or eliminating tumors. The spheres can also incorporate radioactive elements that provide local radiation therapy.

A fifth example of a multi-component medium includes small beads or spheres (microspheres) used to deliver gene therapy to tissues. Microspheres may be used to deliver gene therapies to solid tumors either through direct injection into tissue or through intravascular delivery into the vessels that feed a tumor. See: Dass, C. R., et. al., "Microsphere-Mediated Targeted Gene Therapy of Solid Tumors", Drug Delivery, Volume 6, Number 4, 1 Oct. 1999, pp. 243-252 (10). Gelatin or other microspheres may also be used as vectors to deliver gene or protein therapy into tissues for angiogenesis, or other regenerative medicine therapies. Administration routes include antegrade arterial injection, retrograde venous injection, and direct injection into tissue. The use of gelatin microspheres may offer some advantages over the use of viral vectors for delivering gene therapy agents, which may include additional regulatory concerns over the use of viral delivery vectors for gene therapy administration. See: Hoshino, K, et al., "Three catheter-based strategies for cardiac delivery of therapeutic gelatin microspheres", Gene Therapy (2006) 13, 1320-1327. Microspheres for gene therapy delivery may also be made of biodegradable polymers that encapsulate the functional gene therapy vector. See U.S. Pat. No. 6,048,551.

In such multi-component mediums and similar mediums, it is common that one material is more dense than the other, and that some separation of the two materials occurs as a result of gravity. The rate of separation depends upon many factors, including, for example, differences in the densities, the size of the particles or agglomerations of particles, and the viscosity of the fluid(s) involved. Other factors that influence the rate of separation include the type of fluid, i.e. Newtonian or non-Newtonian, as well as particle to particle and particle to container interactions.

To improve or maintain consistency of delivery, it is desirable to either prevent this separation or to resuspend the components if significant separation does occur.

U.S. Patent Application Publication No. 2001/0018571 discloses a device that provides a suspended agent without additional mechanical mixing to affect resuspension. That device divides a total volume of a sedimenting agent into a network of sub-volumes and includes ports for an inflow and an outflow of a propellant fluid to releases the sub-volumes of agent from the device.

There are a number of patents which disclose separately storing and then uniformly mixing two materials, often a powder and a liquid, with the desired result of uniform mixing, dispersion, or dissolution of one material into the other, with subsequent dispensing or delivery. Among these are the following references: U.S. Patent Application Publication Nos. 2004/0127846 and 2004/0092883; and U.S. Pat. Nos. 6,699,214; 3,951,387; 4,808,184; 4,172,457; 5,425,580; 5,810,773; 5,908,054; 6,062,722; 5,176,446; 6,432,604; 6,814,482; 5,385,564; 5,120,135; 3,370,754;

3,477,432; 3,606,094; 5,354,285; 5,779,668; 3,373,906; 5,071,040; 3,831,903; 5,240,322; 4,704,105; Re. 32,974; 5,275,582; 4,543,094; 7,244,248; 6,706,020; 6,726,650; 6,758,828.

U.S. Pat. No. 6,575,930 discloses a number of devices, systems and methods to facilitate or to improve the initial creation and/or mixing of, for example, contrast medium, and to agitate the contrast medium to maintain a relatively uniform distribution of the contrast enhancing agent or particles throughout the liquid contrast medium prior to and/or during an injection procedure.

The agitation mechanisms or devices of U.S. Pat. No. 6,575,930 can be categorized broadly in three classes which can be used separately or in combination. In the first class of agitation mechanism, the contrast medium is agitated by bulk movement of the entire storage volume or container in which the contrast medium is prepared and/or kept prior to and/or during injection into the patient. The second class of agitation mechanism agitates the contrast medium within the storage volume or container without bulk movement of the storage volume or container. The third class of agitation mechanism agitates the contrast medium by circulating/transporting the contrast medium using an agitation pump. For example, the contrast medium can be transported between two storage volumes or containers in an alternating manner.

Cell therapies as described above involve delivery of living cells (for example, single cells, agglomerations of cells, or cells on microcarriers or scaffolds). The delivery of live cells provides a number of unique challenges in regards to maintenance of a suspension or resuspension. See, for example, Wong, K. et al., Overview of Microcarrier Culture, Cellular Bioprocess Technology, University of Minnesota, 1-8 (2004). For example, cells can be damaged if the shear rate in the fluid is too high. Dewitz et al. reported significant effects on white cells in the stress range of 100-300 dynes/cm.sup.2 and nearly complete destruction at 600 dynes/cm.sup.2. Dewitz, T S, Hung T C, Russel R M, McIntire L V. Mechanical Trauma in Leukocytes. Journal of Laboratory and Clinical Medicine. 90: 728-736 (1977). The effect of stress is also time dependent. See, for example, Kameneva, M. V. et al., Effects of Turbulent Stress upon Mechanical Hemolysis: Experimental and Computational Analysis, ASAIO Journal, 418-423 (2004). The delivery of cells and some of the unique challenges associated therewith are also discussed in PCT Publication Nos. WO 2007/056247 and WO 2007/053779.

Further, there are some indications that significantly lower stress can damage non-blood cells. See, for example, Mardikar, S. H. and Niranjan, K., Observations on the Shear Shear Damage To Different Animal Cells In a Concentric Cylinder Viscometer, Communications to the Editor, Biotechnology and Bioengineering, 68:6, 697-704 (2000). Moreover, damage that is not immediately lethal or destructive of cells can cause significantly shortened lifetimes. See, for example, Blood Cell Damage by Artificial Organ Devices is Focus of University of Pittsburgh Scientists Talk at International Congress of Biorheology, News Bureau, University of Pittsburgh Medical Center (UPMC), 1-3.

Cells also tend to have higher cohesion and adhesion than, for example, ultrasound contrast bubbles and inanimate particles such as embolization spheres. In addition, if cells are killed, their DNA and other cellular components may be released, and the DNA and other cellular components, being relatively long molecules, are "sticky".

Multi-component injection mediums with cells and some type of cell substrate, scaffold, beads, or support spheres are more difficult to maintain in suspension as a result of several of the factors mentioned above.

In addition, especially for multi-component injection mediums, cells, or cells on carriers being delivered to tissue, it is desirable to have a concentrated slurry, often as concentrated as is reasonably achievable, in contrast with applications for contrast or drug delivery where the medium is being delivered into blood vessels and some extra water or liquid is minimally detrimental.

It is thus desirable to develop resuspension devices, systems, and methods suitable for use in cell therapies which creates a sufficiently flowable slurry or suspension of a consistent concentration and flow properties. Such devices, systems and methods can also have application to situations beyond cell therapies wherein a multi-component injection medium is to be delivered to a patient.

SUMMARY OF THE INVENTION

In one aspect, the present invention provides a system for delivering a slurry to a patient including a container to encompass the slurry, wherein the slurry includes solids in a carrier liquid. The container includes an outlet. The system further includes a fluidizing system adapted to affect dilation of the slurry while maintaining a supernate.

The system can further include a controller to affect dilation of the slurry while maintaining a supernate. The controller can include a computer or microprocessor. The controller can, for example, be part of an injector adapted to inject the slurry into the patient.

The container can, for example, be adapted to allow settling such that the supernate is formed and to allow dilation of the slurry with a portion but not all of the supernate.

The fluidizing system can, for example, include a conduit having an outlet, the outlet being adapted to be positioned within the slurry to deliver liquid into the slurry in, for example, a pulsatile manner. The conduit can have an inlet in fluid connection with the supernate within the container. In one embodiment, the conduit is a needle in fluid connection with a syringe.

In several embodiments, the conduit is in fluid connection with a vessel other than the container from which liquid can be introduced into the container.

The conduit outlet can, for example, be in the vicinity of the container outlet. In one embodiment, the container includes a second plunger slidably positioned within the container toward the container outlet from the first plunger. The second plunger is slidable within the container independently of the first plunger. The conduit is in fluid connection with a first passage through the second plunger so that the conduit is in fluid connection with a volume between the second plunger and the first plunger. The second plunger further includes a second passage positioned to be in fluid connection with the supernate. The second passage has a one-way valve in fluid connection therewith so that supernate can pass through the second passage into the volume between the second plunger and the first plunger.

The container can include a pressurizing mechanism adapted to pressurize the contents of the container. The pressurizing mechanism can, for example, include at least a first plunger slidably disposed within the container. The plunger can, for example, be adapted to operatively connect to an injector (for example, a powered injector) as known in the art.

In a number of embodiments, the container outlet is positioned radially outward from an axis of the container.

Such a container can, for example, include a pressurizing mechanism adapted to pressurize contents of the container. The pressurizing mechanism can be a syringe slidably positioned within the container. The system can further include a bulk motion system adapted to impart motion to the container. Likewise, the system can further include a stirring system adapted to impart motion to contents of the container. The stirring system can include a moveable element within the container. The moveable element can, for example, be a plunger that is slidably positioned within the container, the plunger being rotatable about an axis thereof. The plunger can be in the form of a screw.

In several embodiments, the system includes a screw pump in the vicinity of the container outlet.

In general, with respect to inducing motion of the multi-component medium/slurry within the container, the motion can be achieved by bulk movement of the entire container. Further, a moving element can be included within the multi-component medium/slurry. Further, fluid can be introduced or circulate using a pumping mechanism.

In another aspect, the present invention provides a syringe including an outlet, a first plunger slidably positioned within the syringe, and a second plunger slidably positioned within the syringe toward the syringe outlet from the first plunger. The second plunger is slidable within the syringe independently of the first plunger. The syringe further includes an extending conduit having a first end toward the syringe outlet from the second plunger and a second end in fluid connection with a first passage through the second plunger so that the conduit is in fluid connection with a volume between the second plunger and the first plunger. The second plunger includes a second passage positioned to be in fluid connection with a volume forward of the second plunger. The second passage has a one-way valve in fluid connection therewith so that fluid can pass through the second plunger into the volume between the second plunger and the first plunger.

In a further aspect, the present invention provides a method for delivering a slurry to a patient including: fluidizing the slurry before delivering the slurry to the patient so that the slurry is dilated while maintaining a supernate. The slurry can, for example, be fluidized a defined period of time before delivering the slurry to the patient. The period of time is preferably less than the time required for the slurry to settle to an extent that substantially interferes with flow thereof.

The devices, systems and methods of the present invention are well suited for use in connection with, for example, slurries including live cells. The live cells can be freely suspended in the carrier fluid or can be incorporated into or onto, for example, microspheres, microcarriers or a matrices which are suspended in the carrier liquid.

The present invention, along with the attributes and attendant advantages thereof, will best be appreciated and understood in view of the following detailed description taken in conjunction with the accompanying drawings.

DETAILED DESCRIPTION OF THE INVENTION

Figures 1A, 1B:
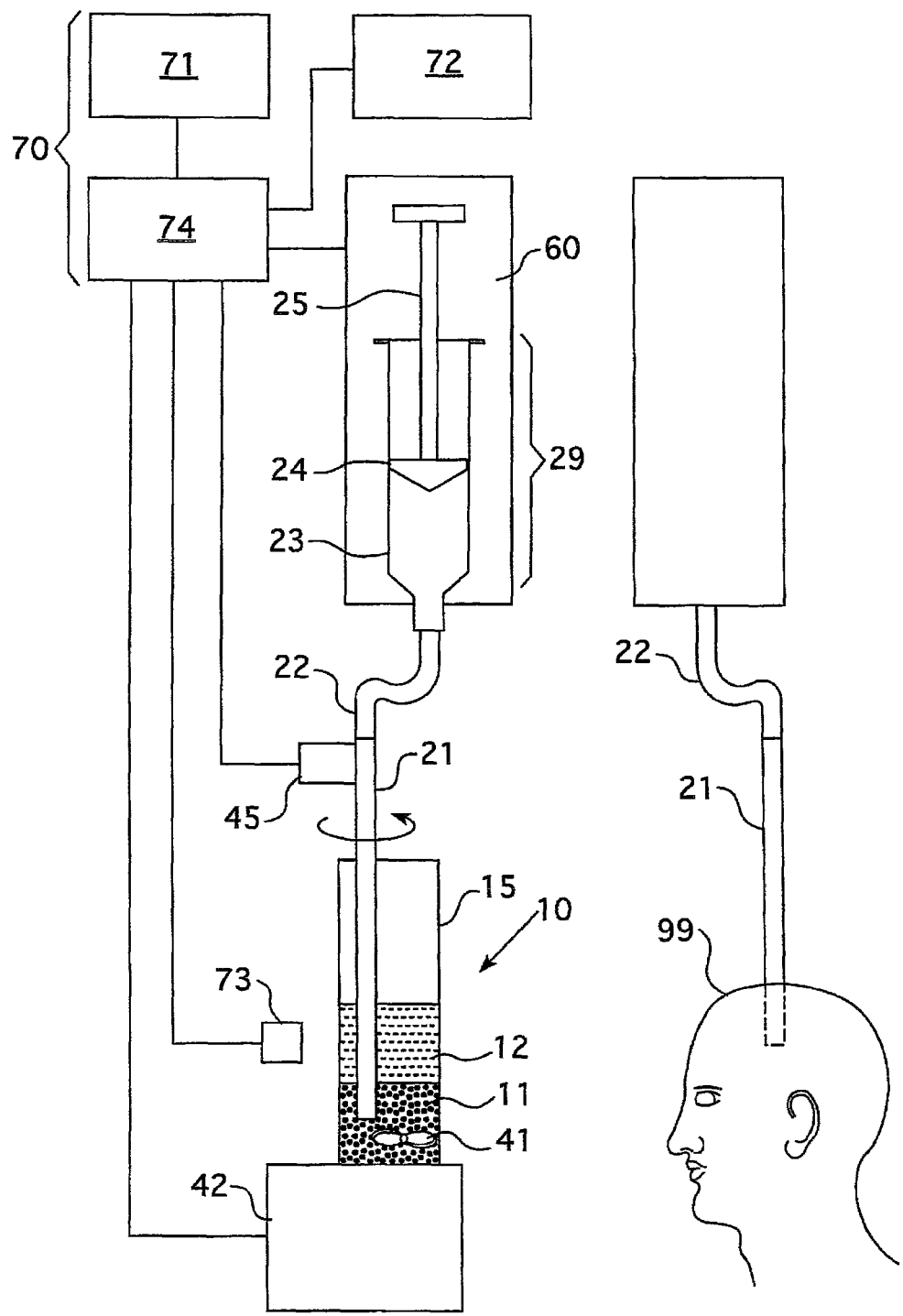
FIG. 1A is an elevational view of an embodiment of a multi-component injection medium resuspension and delivery system of the present invention for use with, for example, a multi-component fluid including spheres or beads, wherein a needle is used to withdraw an amount of resuspended and dilated slurry.
FIG. 1B is an elevational view of a portion of the system shown in FIG. 1A in use for delivering an amount of the slurry to a patient.

In general, the devices, systems and methods of the present invention are applicable to multi-component fluids (and, particularly, slurries including live cells) wherein the components are not totally miscible (at least in the time frame of a delivery procedure in which the fluid is delivered to a patient) and there is a tendency for the components to separate over time.

In general, the term slurry is used to describe solids or immiscible particles carried along in a liquid or carrier liquid. In many cases, the solids will settle relatively quickly if, for example, flow or circulation is low or stopped. Phenomena associated with slurries are reviewed by Iverson, S. M. and Franks, G. V, in Particle Technology Demonstrations For the Classroom and Laboratory, Chemical Engineering Education, 274-280 (Fall 2003).

Solid, insoluble particles are typically heavier than the liquid. Solids settle, leaving behind a supernate having a higher than average fraction of the liquid component. Most slurries, like sand or other minerals in water, do not have significant adhesion between the particles. Some clay or very fine particles may exhibit significant adhesion.

For a slurry to flow, the average separation between the slurry particles must increase in comparison to that in the settled state. Correspondingly, the volume of the settled slurry must expand. This expansion requires that liquid move from the supernate into the settled slurry. This phenomena is referred to as dilation. Dilation is discussed in Particle Technology Demonstrations for the Classroom and Laboratory by Simon M. Iveson, George V. Franks of the University of Newcastle Callaghan, NSW 2308, Australia as published in Chemical Engineering Education Fall 2003, pp 174-280.

If a settled cell (optionally, associated with microcarriers) slurry is pressurized, motion will not occur until the drag on the particles from the fluid flowing around the particles is sufficient to break the adhesion and/or cohesion of the slurry particles with each other and with the walls of the container and dilation occurs.

The resuspension or mixing in the present invention is adapted to achieve a sufficient resuspension or dilation so that the slurry can flow through the fluid path elements and into the patient. However, the resuspension is not necessarily meant to create a totally uniform dispersion within the whole storage or delivery volume, as is typically the goal in other agitation or mixing systems used in delivery of agents to patients. It is acceptable and even desirable that there be extra liquid or supernate remaining after the slurry is delivered. If the slurry is dilated to too great an extent, then extra liquid is delivered with the therapy, and this extra liquid may limit the dose that can be given, may lengthen the procedure by requiring multiple cycles of dosing with time for liquid diffusion in between doses, may carry the therapy to adjacent tissue which is not the target, or may cause a buildup of pressure in the tissue that can force the therapy out the needle tract or some other path, and thus cause it to be wasted. In general, it is desirable to create a substantially uniform concentration or distribution of solids within the fluidized slurry just sufficient to provide consistent injections (particularly over multiple injections). However, it is not typically desirable to affect a uniform concentration or distribution of solids within the total volume of fluid within the vessel, container or conduit (that is, it is not typically desirable to eliminate all the supernate).

FIGS. 1A and 1B illustrate an embodiment of a relatively simple multi-component injection medium resuspension and delivery system of the present invention for use, for example, with a multi-component fluid 10 including cells on spheres or beads 11. The multi-component injection medium 10 is held in a container 15. The heavier component, the spheres or beads 11 in this example, of the multi-component injection medium 10 will settle over time toward the bottom of the container 15 and leave some amount of free liquid 12 above the heavier component.

To resuspend the beads 11, a needle 21 is inserted into the settled beads 11 and is gently agitated. This can be accomplished manually or mechanically and automatically (by, for example, moving the needle with a motorized holder 45 and/or by moving the container 15 through a motorized holder) to effectively stir the contents. Alternatively, a separate stirring mechanism, such as stirring element 41, can be incorporated in the container 15. The stirring element 41 may be moved by a motion-inducing element 42 in relation to the container 15 and the slurry 11 therein. Alternately, the motion-inducing element 42 could move the container 15 itself with respect to the needle 21, with or without the presence of the stirring element 41.

Alternately, the stirring element could be attached to the tip of the needle 21 and thus increase the agitation. In this case the stirring element could be, for example, a larger diameter tube or a vaned assembly into which the needle 21 is inserted. In this embodiment, it is preferable that the stirring element be readily attachable and detachable from the needle 21 without compromising the sterility of the fluid medium 10.

The relative motion of the needle 21, container 15, and/or stirring element 41 can be a simple rotational or circular motion. Alternatively, the motion can be more complex or sophisticated. For example, a precessing circular motion, a precessing figure eight motion, or other more complex motions can be used. The speed of motion can be relatively slow so as to reduce the sheer damage to the slurry 11.

During agitation, the volume of the settled beads 11 expands slightly by incorporating some of the free liquid or supernate 12. As mentioned above, this slurry behavior phenomena is called dilation. Dilation occurs because the beads 11 need to separate more than in the settled state for one bead to be able to easily move past another bead. When the slurry containing medium 10 is sufficiently resuspended (for example, after a preset time has elapsed, upon visual inspection by an operator, or as determined by a physical sensor system 73—for example one that measures the force of resistance to agitation, density of slurry, or amount of dilation, for example, by light or sound reflection, absorbance, or transmission), the pump 60 is activated to pull the beads 11 of slurry 10 from the container 15 into the fluid path. The fluid path in this example includes three fluid path elements: a needle 21, tubing 22, and a syringe 29.

The syringe 29 (and other devices and systems of the present invention) can, for example, be operated by a microprocessor controlled pump 60 controlled by the control unit 70 as known in the art. The control unit 70 incorporates a processing/memory unit 74 and can also include or interact with a user interface 71 so the operator can select and ensure proper operation. The control unit 70 can also include a communications interface 72 through which it can communicate with other medical equipment, for example imaging equipment or hospital information systems as discussed in U.S. Pat. No. 6,970,735. The control unit 70 can also include or is in communication with optional sensor(s) 73 to assess the state of the slurry 10.

The pump 60 (which is the pressurizing mechanism in this embodiment) creates a negative pressure to pull the slurry 11 from the container 15 into the needle 21, and optionally into tubing 22 and syringe 23, depending upon the volumes of the various fluid path elements and the volume to be contained in the dose. It is preferable that there be relative motion of the needle 21 with the injection medium as the medium is withdrawn. Otherwise, the beads or slurry particles 11 can be depleted from a region around the needle tip and after pulling a little of the slurry 11, primarily free liquid 12 will be pulled into the needle tip, causing an inaccuracy or inconsistency in the dose. The inside diameter (ID) of the needle 21 and the tubing 22 can preferably be several multiples (for example, >4) larger than the mean diameter of the beads 11, to enable free flow. It can also be desirable, although not required, that the ID not be too large (for example, <10 times larger the mean diameter) to reduce the likelihood of significant settling and clumping in the fluid path.

Alternative or additional stirring or agitation mechanisms to achieve resuspension or dilation that can be adapted for use with the system of FIGS. 1A and 1B are described herein in relation to alternate containers.

After a dose is agitated or stirred to achieve dilation or resuspension, and pulled into the fluid path element(s), the needle 21 is withdrawn from the container 15, and the fluid path 21, 22, 29 is prepared for delivery into the patient 99. In the example of SPHERAMINE, the delivery can be through the same needle 21 using a stereotactic frame to guide the needle's insertion into the brain of the patient 99. In the case of embolization spheres, the needle 21 may be disconnected and the syringe 29 and tubing 22 connected to a catheter (not shown) that has been placed in the desired blood vessel. Alternatively to a needle, a sufficiently rigid piece of tubing can be used, which is then removed or is connected to the luer connection which is standard on catheters.

The pump 60 is then activated by the user and the control unit 70 ensures delivery of the multi-component injection medium 10 to the patient 99 using the user programmed, preprogrammed, or system feedback determined dose volume, flow rates and other delivery parameters. A system similar to that of U.S. Pat. No. 5,840,026 can be used, which employs the operator in a feedback loop to control the delivery of the multi-component injection medium 10.

The embodiment of FIGS. 1A and 1B provides several benefits. For example, the geometries of the container 15, the fluid path elements 21, 22, 29, and the motions thereof can be readily determined to provide sufficient agitation for resuspension while avoiding or minimizing cell damage. The determined conditions can then be programmed into the control unit 70 either as a standard protocol or a range of operation parameters so that different sites around the world can achieve the same results and benefits. The system is also flexible. The container 15 and fluid path elements 21, 22, 29 can, for example, be of varying sizes and geometries for use with various treatments or products.

The device and system of FIGS. 1A and 1B can be considered to consist of a container 15 to hold a slurry 11 and excess supernate 12, a fluidization or agitation means 21, 41 powered and controlled by a control unit 70, a user interface 71 to program the control unit, a sensor means 73 for determining when the agitation is sufficient, and a means to deliver the slurry 11, including fluid path elements 21, 22, 29 and at least one pump 60. There are additional optional device or system components described elsewhere herein, for example, a communications interface 72.

A potential drawback to the system of FIGS. 1A and 1B is that the container 15 is periodically open to the air when the needle 21 is inserted into the slurry 11. To reduce the chance of contamination by airborne contaminants, the system can be operated in a laminar flow hood or within an operating suite area with laminar air flow. Alternately, a cap or labyrinth (not shown) can be use to reduce the potential of contamination. Moreover, the needle 21 can be required to pierce a rubber septum (not shown) that seals the slurry 11 from contamination. The septum can be wiped with a disinfectant before use.

There are a number of alternative devices embodiments in which the multi-component injection medium 10 is contained in a closed system for resuspension, dilation, and delivery. In these embodiments, the slurry 11 is pumped directly from the storage container or reservoir for delivery to the patient.

The agitation and resuspension devices and systems disclosed in U.S. Pat. No. 6,575,930 can be used with many injectors and injector systems other than those set forth therein and can be modified for use in resuspension of multi-component fluid mediums, such as slurries (for example, including living cells). For example, a simple spring-powered syringe pump that runs at a constant rate can be used as an injector. The user interface may, for example, have only start and stop capabilities. Indeed, an external source of power is not required. In that regard, a person could be part of the injector system and may perform many of the functions described above. A person, for example, can manually operate a syringe. Mechanical injectors, however, are better able to perform injections consistently and precisely.

In general, many of the devices, systems and methods of U.S. Pat. No. 6,575,930 can be modified for use in delivery of slurries including live cells. In that regard, one can modify flow rates, orifice sizes, geometry specifics and other parameters based upon the specific cells, carriers, beads, and/or spheres being delivered. For example, the inner diameters (ID) of the outlet and the tubing that carry slurry can be sized to allow for passage of the spheres or carrier beads (for example, to have an inner diameter greater than four times the bead diameter). Further, the flow rates and inner diameters are such that the shear forces developed are below a threshold shear force above which significant damage to the cells occurs. Sufficient fluid should be provided to allow for dilation. Moreover, as set forth above, operation preferably occurs with sufficient flow/agitation that the slurry is dilated for flow, but not uniformly mixed to the point that it is too dilute to be optimal when delivered.

Figure 2A:
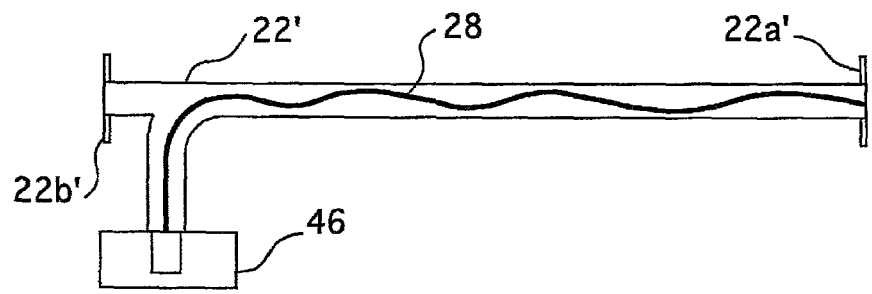
FIGS. 2A and 2B are elevational views that illustrate the use of a moveable element to affect resuspension in a conduit.
Figure 2B:
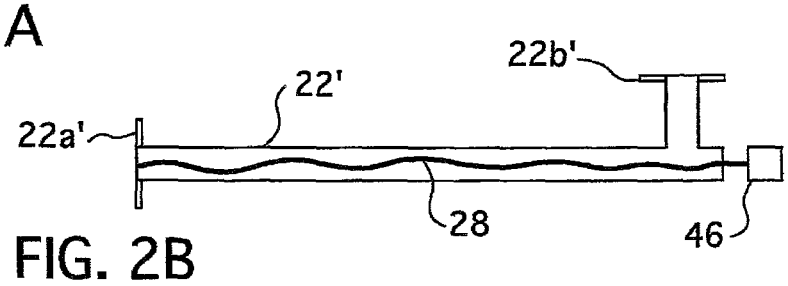

FIGS. 2A and 2B illustrates a section of a volume or an element 22' of the fluid path (for example, tubing 22 or other conduit of a container such as a syringe 29) including a wire, helical element or other movable element 28 that can be rotated, reciprocated, vibrated or otherwise moved within the tubing or fluid path element 22' to impart motion to a slurry therein. A motorized stirrer 46 on the end of a shaft can also be used. Also a stirrer 28 that is moved without a connected shaft (for example, a magnetic stirrer as known in the art) can also be used. A plurality of moveable elements 28 can be included in a container (for example, syringe), tubing, and or other conduit. In the case of a syringe including one or more plungers, motion of one or more of the plungers can be used to suspend, dilate, or resuspend a slurry.

Motion can also be imparted to a slurry within a volume by imparting motion to the container, tubing or the conduit defining or bounding the volume. For example, a volume can be rotated. The rotation can be slow, wherein settling as a result of gravity causes continual agitation. Moderate rotation can prevent settling such that particles are always "falling" but never reach the "bottom". Quicker rotation can create currents within the fluid of the volume that maintain the suspension. A rocking motion can also or alternatively be used. The volume can also be vibrated or moved in a precessing motion. In several embodiments a miniature or subminiature vibratory motor, such as used in a "vibrate" mode of cellular phones, can be used. A sudden flick or other shocking motion can also be applied to a volume.

Suspension or resuspension can also be affected by fluid flow. For example, FIGS. 3A-4B illustrate systems wherein the multi-component injection medium 10 is generally contained in a syringe 29 or other container or volume.

Figure 3A:
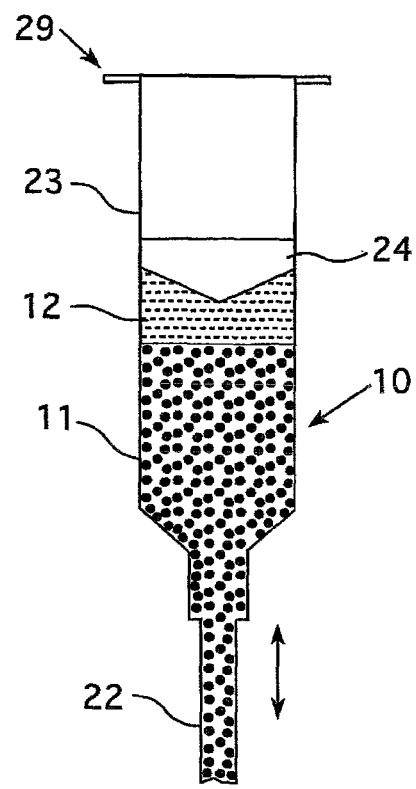
FIGS. 3A and 3B are elevational views that illustrate the use of mechanical vibration and oscillating flow to affect resuspension.

In FIG. 3A, the syringe 29 is oscillated, generally slowly up and relatively more quickly down. If the density difference between the settling component (e.g., beads or spheres) 11 and the supernate 12 is sufficient, the rapid downward motion will dilate the slurry.

Figure 3B:
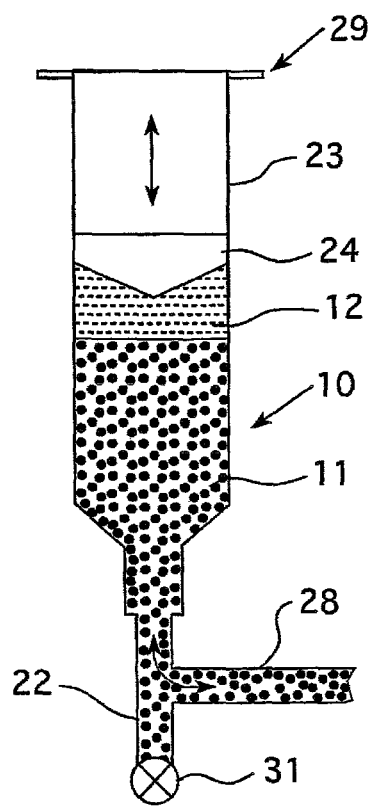
Figures 4A, 4B:
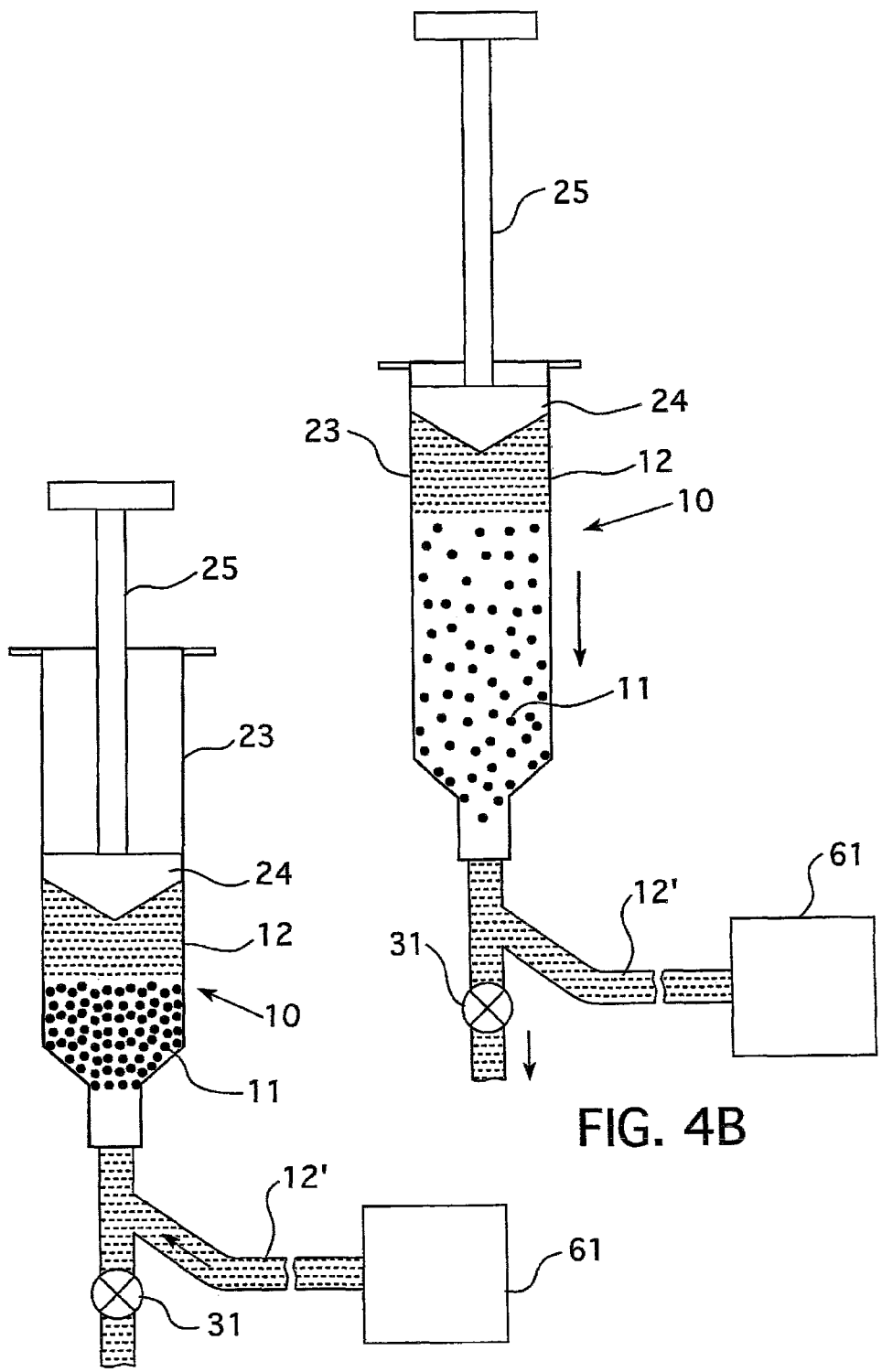
FIGS. 4A and 4B are elevational views that illustrate dilation of a slurry using fluid injected into a syringe from another source of fluid.

In FIGS. 3B, 4A, and 4B, before dispensing, or periodically in time, fluid flow enters the syringe 29 at the bottom of the vertical syringe to agitate, disrupt, and fluidize the slurry 11. Then the multi-component injection medium 10 can be delivered with a more uniform/consistent concentration, density and flow characteristics. In FIG. 3A, reciprocating pressure waves and/or reciprocating flow are used to suspend or resuspend a slurry 11. If there is plunger motion, as indicated in FIG. 3B, it is preferable that the forward (expelling) motion pushing the supernate 12 through the settled slurry 11 and out of the syringe be slow, so that the supernate 12 moves through the slurry 11 with the exertion of minimal force. Then when the syringe 29 operates in the reverse direction, pulling in fluid, that this be done more quickly so that the settled slurry 11 is dilated by the forces of the flow of the liquid.

In FIG. 4A, a reverse flow of additional supernate 12' is used to "break up" or resuspend the settled slurry 11. The resuspension can, for example, be performed shortly before use or delivery of the slurry 11 to the patient. The additional supernate 12' can be pushed in by a pumping element 61 controlled by the control unit 70, or alternately it can be stored in a reservoir and pulled in by the motion of the syringe plunger 24, similarly controlled by the pump 60 and the control unit 70 with valve 31 closed. The resuspension can also be performed periodically. The process is similar to fluidization of a fluidized bed. The dilated or suspended slurry 11, optionally with surplus supernate 12 above it, can then be delivered to the patient by moving the syringe plunger 24 forward with, for example, pump 60 (not show in this figure).

In "Flow through Packed Beds and Fluidized Beds," by R. Shankar Subramanian, the author shows how a settled bed can be dilated or fluidized by flow, and that if the flow is slowed gradually, the bed remains in a relatively dilated state compared to its starting state. Applying this knowledge to the current embodiments, a preferred flow rate profile for pulling fluid into the syringe 29 (as, for example, in FIGS. 3A-4B) would begin with a rapid rise flow rate to that sufficient to dilate the slurry 11, and then a gradual reduction in flow rate so that the slurry 11 resettles in a relatively dilated state. It this state it is either possible for forward flow out of the syringe to easily move the slurry 11, or for it to be more easily dilated subsequently as needed.

Whether the slurry bed breaks apart under specified conditions (for example, flow rate, volume, duration) is optionally an indication of cohesion and thus optionally of the suitability of the fluid 10 for delivery to the patient. If the slurry does not break apart at the first settings, optionally there can be additional attempts at the same or alternative settings. If the slurry fails to dilate and become flowable as judged by the operator or by sensors, then this slurry batch can be declared unfit for injection and the preparation procedure repeated from the appropriate point with a new slurry batch.

Fluid from one portion of the syringe, vessel, conduit (or other volume) can also be charged, pumped or moved to another portion thereof to affect dilation, suspension, or resuspension. For example, the system of FIG. 5 fluidizes a slurry 11 by pulling supernate 12 from the mixture and injecting it near the outlet to resuspend the slurry 11. The syringe or system of FIG. 5 includes a first, rearward or upper plunger 24a slidably positioned therein and a second, forward or lower plunger 24b positioned therein that is slidable independent of the first upper plunger. For example, a plunger rod 25b of the lower plunger can include extending members that pass through the upper plunger 24a in a sealed manner. Alternately, the plunger rod 25b of the second plunger 24b can also extend through a passage in the center of the plunger rod 25a of the first plunger 24a.

The lower plunger 24b includes a first passage 211 therethrough to provide fluid connection between a first volume 201 between the upper and lower plunger and a second volume 202 below or forward of the second plunger. A first end of a conduit 210 is in fluid connection with the first passage 211. A second end 212 of the conduit 210 preferably extends to the vicinity of or within the slurry (for example, in the vicinity of the outlet of the system) to enable fluidization of the slurry 11. The conduit 210 preferably contains or incorporates a one way valve 31' or check valve so that fluid can only flow though the conduit from the first volume 201 toward the second volume 202. The second plunger 24b also includes at least a second passage 220 between the first volume 201 and the second volume 202. A one-way valve or check valve 31" is preferably in fluid connection with the second passage 220 so that fluid can flow from the second volume 202 to the first volume 201 through the second passage 220, but fluid cannot flow from the first volume 201 to the second volume 202 through the second passage.

Figure 5:
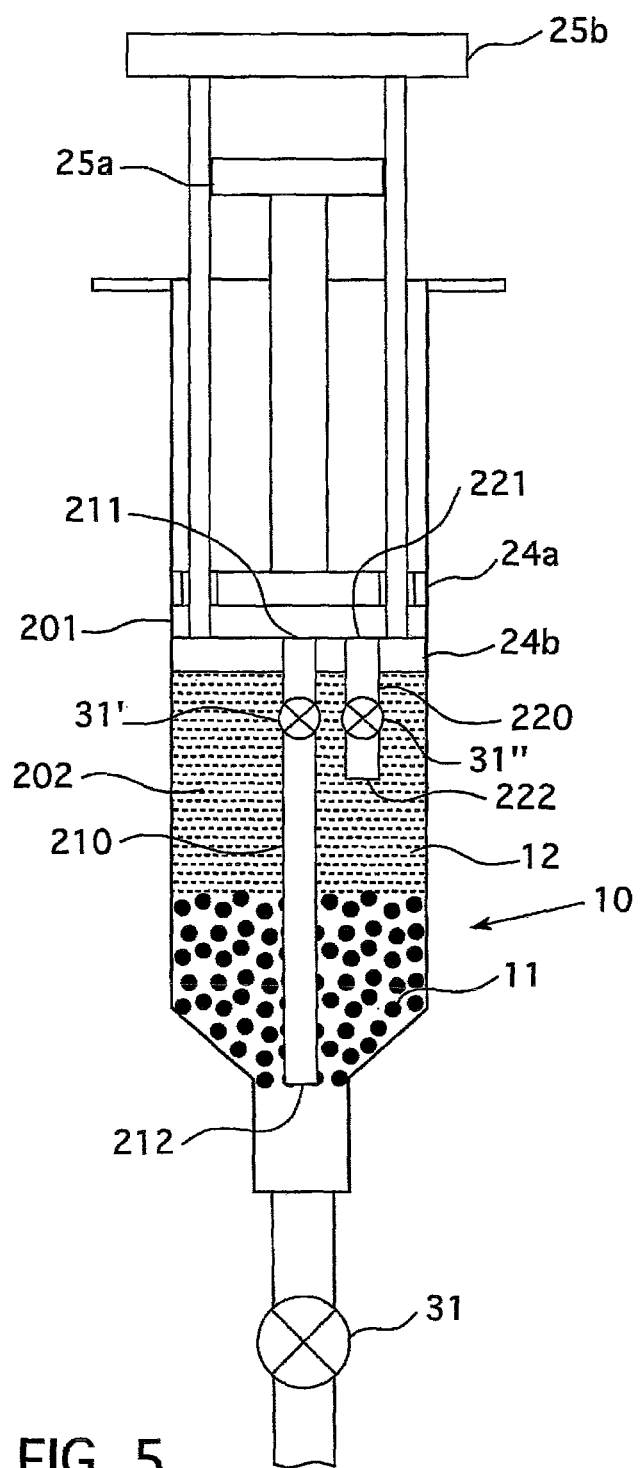
FIG. 5 is an elevational view that illustrates an embodiment of a system of the present invention in which movement of a forward plunger is used to affect resuspension.

During operation of the system of FIG. 5, the lower plunger 24b is first is moved downward (toward the outlet) to fill the space between the two plungers 201 with supernate via the second passage 220. The lower plunger 24b can then be moved upward (away from the outlet) to expel the supernate 12 out the second end of the conduit 212, near the neck/outlet region of the system/syringe, thereby fluidizing or dilating the slurry. When desired, the upper plunger 24a (and optionally lower plunger 24b) can be moved downward to expel/deliver the fluidized slurry 11.

Figure 6:
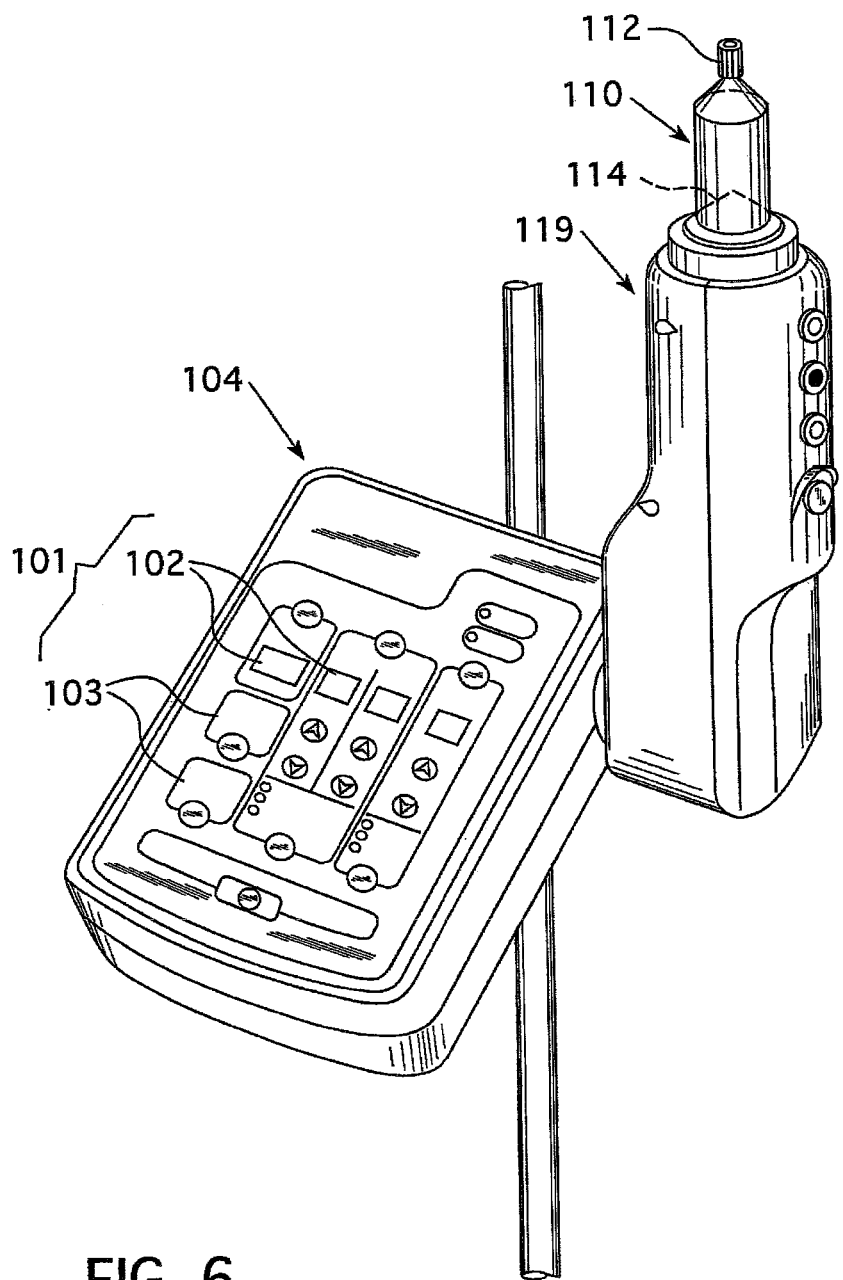
FIG. 6 is a perspective view that illustrates an embodiment of an injector system (including an attached syringe) of the present invention in which the orientation of the syringe is changeable to affect resuspension.

In one embodiment, a syringe 10 (similar to the syringe illustrated in FIG. 1B of U.S. Pat. No. 6,575,930) illustrated in FIG. 6 of the present application is oriented with a neck 112 of the syringe 110 in an upward orientation. In this orientation, the slurry settles against a plunger 114 slidably positioned within syringe 110. Shortly before delivery, the syringe pump mechanism 119 can be rotated so that syringe neck 112 is pointed in a downward direction and so that the slurry breaks up as it falls to neck 112. For some time, dependent upon the specifics of the cells, beads, and other components involved, the slurry will be in an easily flowable state ready for delivery. If a delivery is completed, or not made within the optimum time, syringe 110 can be returned to the "neck up" position, again breaking up the slurry and readying it for the next cycle of syringe motion and delivery.

Figure 7:
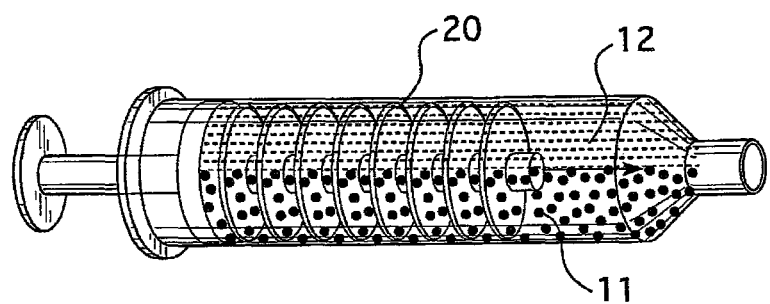
FIG. 7 is an elevational view that illustrates an embodiment of a system of the present invention in which a screw-shaped plunger in the container (syringe) is rotated to resuspend a slurry within the container.
Figure 8:
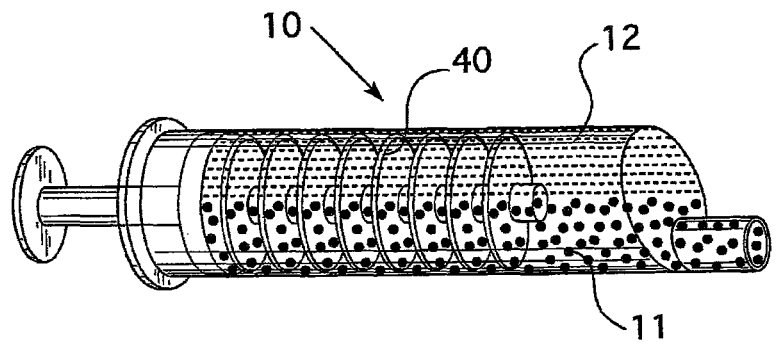
FIG. 8 is an elevational view that illustrates an embodiment of a screw-shaped or helical magnetically-coupled stirrer positioned within the container (syringe) to resuspend a slurry within the container.

In a generally horizontal syringe (or other horizontal volume or container), one can incorporate a stirring or moving element as described above. The moving element can, for example, rotate before dispensing to fluidize the slurry. A plunger can then be advanced forward through the volume to dispense the slurry. In FIGS. 7 and 8, the slurry is dispensed as a result of pressure built up within the syringe (or other volume). In FIG. 7, a screw-shaped plunger 20 in the container is rotated to suspend or resuspend a slurry 11. The plunger 20 is advanced toward the outlet to expel the mixed slurry 11. In FIG. 8, a screw-shaped or helical magnetically-coupled stirrer 40 is positioned within the container (syringe) to suspend or resuspend a slurry within the container. An outlet is positioned at the "bottom" of the generally horizontally oriented container. This is so that the fluidized or dilated slurry 11 can be delivered without the excess supernate 12. The slurry is pressurized via advancement of a plunger through the container toward the outlet.

Figure 9:
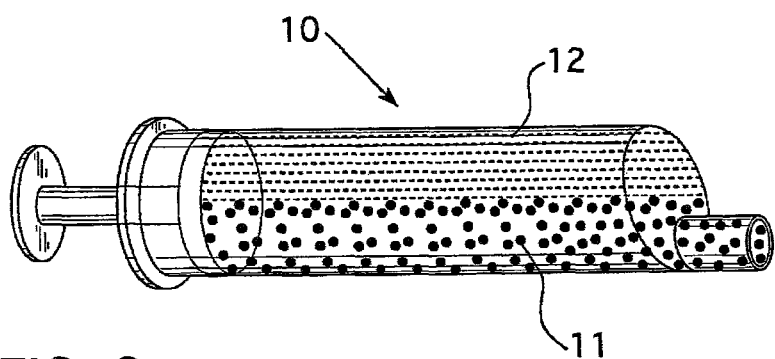
FIG. 9 is an elevational view that illustrates an embodiment of a horizontally-oriented container in which an outlet is positioned to affect resuspension in a slurry near the outlet.

FIG. 9 illustrates a generally horizontal syringe with no stirring element. The outlet end of the syringe is positioned so that, as fluid is expelled, some of the supernate is forced to flow through the slurry as it exits the syringe, fluidizing the slurry as it moved. In general, significant agitation and dilation only occurs in the slurry very near the exit. The remainder of the slurry is simply pushed as a settled slurry along the surface of the syringe.

Figure 10A:
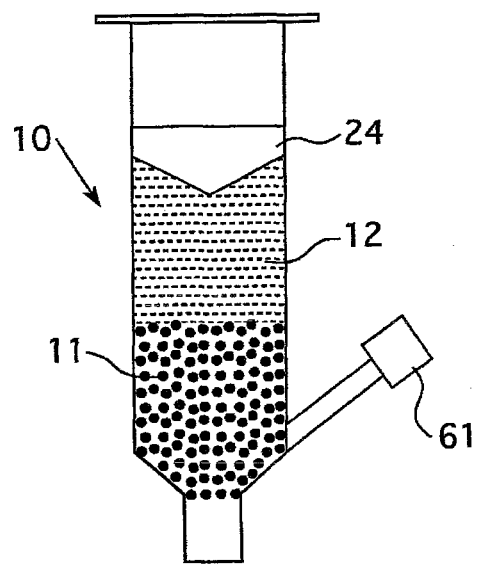
FIGS. 10A-10C are elevational views that illustrate an embodiment of a system in which supernate or liquid from a separate reservoir or source is injected as the slurry is dispensed to fluidize the slurry and provide the liquid for dilation.
Figure 10B:
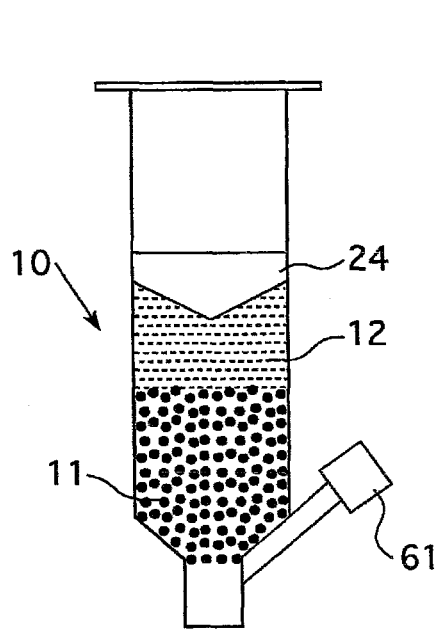
Figure 10C:
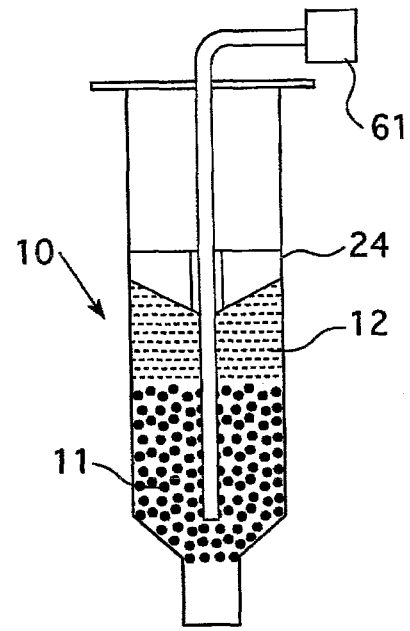

In the systems shown in FIGS. 10A-10C, supernate or liquid from a separate reservoir or source (not shown) is injected as the slurry 11 is dispensed to fluidize the slurry 11 and provide the liquid for dilation to enable flow. The container is pressurized (for example, via a plunger 24) to dispense the fluidized slurry 11. This has the advantage that the amount or proportion of supernate added to the settled slurry 11 can be easily varied or controlled by controlling the relative flow rates of the syringe and the auxiliary pump 61.

In all of the systems disclosed herein, the fluid flow is not limited to being unidirectional or of a constant flow rate. Typically, high flow rates better fluidize a slurry, but also cause higher shear stresses in, for example, the narrow segments of the fluid path. Therefore, a pulsed or pulsatile flow pattern can provide benefits (either in a single direction or with flow reversal). There is also a benefit to a flow profile wherein the flow actually reverses direction, at least in some of or the majority of the fluid path. In this case, the reverse flow preferably draws liquid from a separate reservoir or from the supernate fluid and not from the patient.

Figure 11A:
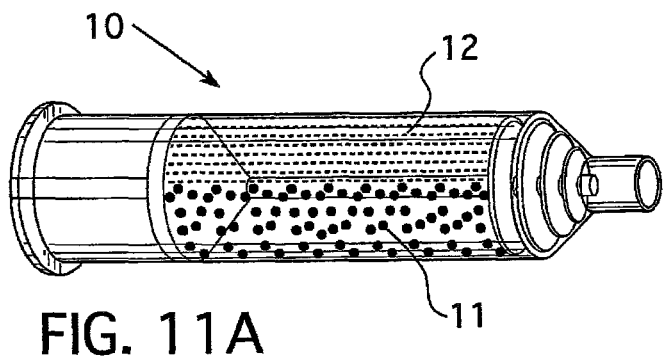
FIGS. 11A and 11B are elevational views that illustrate an embodiment of a screw pump element incorporated into a fluid path element or volume (for example a syringe or tubing) to drive, for example, SPHERAMINE®, into an attached conduit (not shown).
Figure 11B:
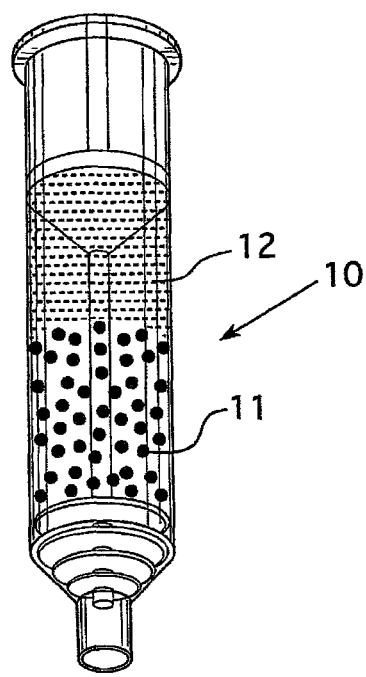

FIGS. 11A-11B illustrate a screw pump element incorporated into a fluid path element or volume (for example a syringe or tubing). When the screw pump is turned, there is a force driving the slurry out of the fluid path element generally independent of the flow of the supernate 12, which is controlled in this example by the displacement of the syringe plunger 24. The dilated slurry 11 then flows into the patient. If the fit between the turning screw element and the inner diameter of the fluid path has a sufficient amount of clearance, there will be sufficient mixing and motion of the supernate 12 to suspend or resuspend the slurry 11. This is especially useful where there is a significant reduction in the inner diameter of the fluid path, to prevent clumping or jamming of slurry at the transition.

Because different slurries will have different properties, and the same slurry can have different properties from batch to batch, and these can not be a priori known, an added benefit of the devices, systems, and methods described herein is that they enable a user to selectably, controllably, repeatably, standardizably, and transferably determine the range of conditions and parameters that will sufficiently resuspend or dilate the specific slurry which they are using. Different system operating parameters can be utilized, for example, in a design of experiments format or with multivariate analysis, to determine the operating range of the parameters that provides sufficient dilation with sufficiently low damage to the slurry. While it may be sufficient in the prior art to use hand agitation when the goal is to fully mix a mixture, hand agitation cannot be repeatable over time nor is it standardizable between people. Thus it cannot be the method or system used to find, let alone to optimize, the parameters for slurry dilation or resuspension.

The devices, systems, and methods of this invention can also be applicable to situations where thorough or uniform mixing are desired, as was the case in many of the prior art patents cited above. The improvements that this invention brings are those heretofore stated, namely, improved and precise selectability, controllability, repeatability, standardizability, and transferability in determining the range of conditions and parameters that will sufficiently mix the mixture in the minimum time, or with the minimum energy, or to an optimum or sufficient state. The prior art examples do not provide as complete an integrated or automated system as does this invention, which includes, for example, a container for the mixture, a powered agitation means, a controller, a user interface to select the agitation conditions, a memory as part of the controller to retain agitation conditions and to support repeatability, standardization, and transferability, a delivery means, and optionally a sensor to assess the agitation.

There are alternatives to providing a controlled system to dilate or resuspend a slurry for delivery. Increasing the viscosity of the liquid is operable to lengthen the time required to settle (at formation of a suspension or after resuspension) or to prevent settling. Increasing viscosity can also facilitate resuspension. If the viscosity is sufficient (for example, approaching that of a light syrup (approximately 10 cP)), settling is significantly slowed, and if it approaches that of honey (approximately 1500 cP), settling is effectively halted. While it is difficult to dispense viscous fluids, it is often done with X-ray contrast media using powered injectors manufactured by companies such as MEDRAD, Inc. of Indianola, Pa., the assignee of the present application. Various injectors are described in, for example, U.S. Pat. Nos. 4,677,980; 5,383,858; 5,840,026; 5,873,861; 6,385,483; 6,652,489; and 5,494,036. The pumps are servo driven and have pressure limitations incorporated into their function. Cells can generally withstand high isostatic pressure. Flow rates should, however, be limited to limit the shear forces on the cells, as mentioned above. Increasing viscosity of slurries including live cells is, for example, discussed in PCT Publication No. WO 2007/056247.

Figure 12:
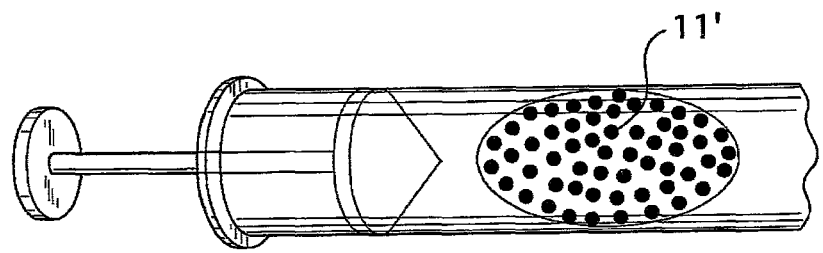
FIG. 12 is an elevational view that illustrates incorporation of cells into or onto a gel bead.

As illustrated in FIG. 12, another approach is to incorporate the cells into relatively solid material, for example, a collagen matrix. This can be thought of as providing a supernate of very high viscosity. In this instance slivers or other shaped volumes of the solid 11' can be injected into the patient using very narrow syringes, which are effectively made by putting solid rods of cells in supernate into hollow needles, and pushing with a rod so as to expel the solid.

The fluidizing system, can, for example, include a conduit having an outlet, where the inlet of the conduit is within the slurry container, and may be adapted to various positions within the container to affect delivery of the part of the slurry that has not yet fully settled. In one embodiment, the conduit is a needle in fluid connection with the syringe, with an inlet portion that may be positioned at various levels within the syringe.

Figure 13A:
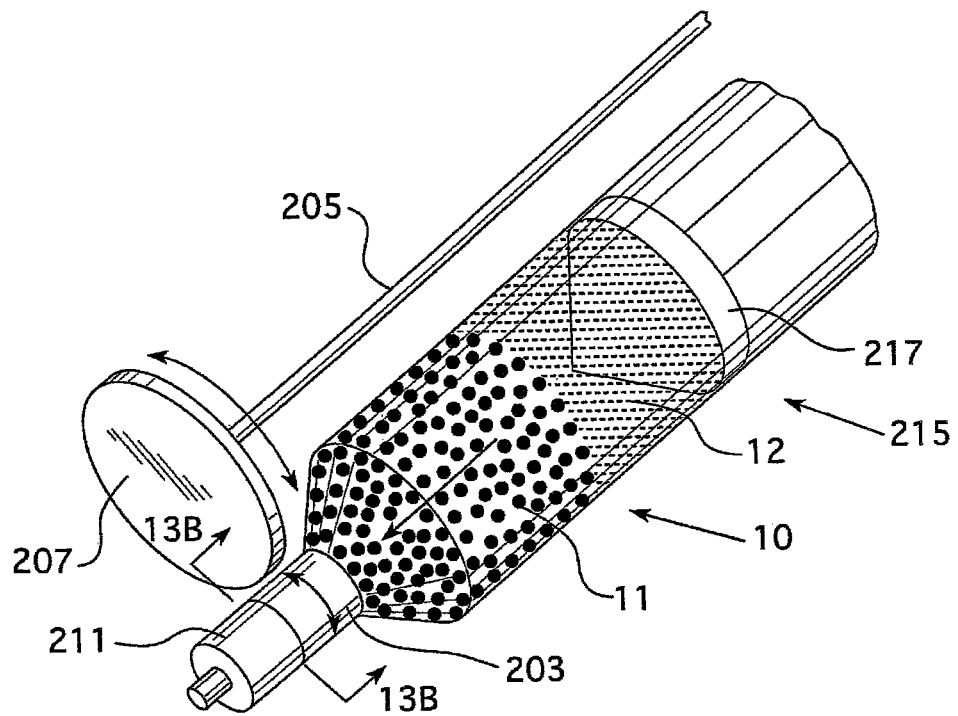
FIG. 13A is a perspective view of yet another embodiment of a resuspension and delivery system of the present invention.
Figure 13B:
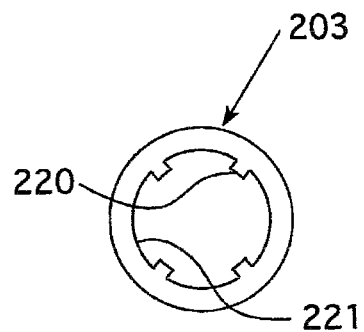
FIG. 13B is a cross-sectional view taken along line 13B-13B of FIG. 13A.

In another embodiment shown in FIGS. 13A and 13B, the fluidizing system may contain an outlet 203 that is moveable with respect to the bulk container 215, such as a syringe. The outlet 203 may be moveable through the use of a sliding seal that is located along the edge or at the end of the container 215. Movement of the outlet 203 (by means of, for example, a motor-driven shaft 205 connected to a disk 207 that engages and moves the outlet 203) with respect to the rest of the container 215 serves to separate the slurry 11 at the juncture of the interface between the container 215 and the outlet 203, serving to loosen the slurry 11 near the interface so that it may be delivered. As the outlet 203 is rotated in a radial fashion, perpendicular to the long axis of the syringe 215, the slurry 11 in the syringe 215 is disrupted near the rotating interface, allowing the slurry 11 to more easily flow when pushed by the syringe plunger 217. The outlet 203 may be rotated in one direction only, or be cycled in a clockwise and counterclockwise manner. In addition, it may be useful to include a second rotating interface 211 so that any motion from the moving outlet 203 is mechanically isolated from any connected tubing or delivery channel (not shown). In addition, the interior surface of the rotating outlet 203 may contain vanes 220, channels 221, or other protruding structures or recesses to increase the mechanical separation of the slurry 11 at the container-outlet interface. Various drive and control mechanisms may be used to optimize the outlet movement speed and timing relative to the container 215.

In general, it is also desirable to select materials for the surfaces of fluid path elements that contact the slurry that are operable or suitably adapted to reduce or eliminate adherence of cells or carrier beads. Examples of materials that inhibit or reduce adherence are electro-polished stainless steel, TEFLON® (a polytetrafluoroethylene material available from DuPont), and other materials know to those skilled in cell culturing and handling.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

The invention claimed is:

1. A system for delivering to a patient a cell-slurry comprising a fluid and cells which are non-dissolvable or immiscible in the fluid, the system comprising:
    a container initially containing the cell-slurry and a supernate of the cell-slurry;
    a syringe adapted to contain the cell-slurry after dilation with the supernate;
    a fluid path between the syringe and the cell-slurry and the supernate in the container, the fluid path comprising a needle at least partially disposed in the cell-slurry and the supernate in the container and tubing fluidly connecting the needle to the syringe;
    a plunger disposed in the syringe and adapted to create pressure in the syringe to cause a dilated cell-slurry contained within the container to flow into the syringe through the fluid path; and
    a fluidizing system comprising a holder adapted to move the needle to affect dilation of the cell-slurry with a portion of the supernate to form the dilated cell-slurry, the holder and the needle imparting agitating movement to the cell-slurry and the supernate in the container to affect the dilation of the cell-slurry with the supernate.

2. The system of claim 1, wherein the holder is a motorized holder to affect the agitating movement of the needle.

3. The system of claim 2, further comprising a control unit in communication with and adapted to control the motorized holder.

4. The system of claim 1, further comprising a stirring element within the container, wherein the stirring element is adapted to agitate the cell-slurry and the supernate in the container to affect the dilation of the cell-slurry with the supernate.

5. The system of claim 4, wherein the stirring element is moved by a motion-inducing element, and further comprising a control unit in communication with and adapted to control the motion-inducing element.

6. The system of claim 1, further comprising a motion-inducing element associated with the container to agitate the cell-slurry and the supernate to affect the dilation of the cell-slurry with the supernate by moving the container.

7. The system of claim 1, wherein the fluidizing system further comprises one or more of:
    a stirring element within the container to agitate the cell-slurry and the supernate to affect the dilation of the cell-slurry with the supernate; and
    a motion-inducing element associated with the container to agitate the cell-slurry and the supernate to affect the dilation of the cell-slurry with the supernate by moving the container.

8. The system of claim 7, wherein movement of one or more of the needle, the stirring element, and the container comprises one of simple rotational motion, precessing circular motion, a precessing figure-eight motion, and combinations thereof.

9. The system of claim 1, wherein the container comprises a pierceable septum, and wherein the needle pierces the septum.

10. The system of claim 1, wherein the agitating movement of the needle comprises one of simple rotational motion, precessing circular motion, a precessing figure-eight motion, and combinations thereof.

11. A system for delivering to a patient a cell-slurry comprising a fluid and cells which are non-dissolvable or immiscible in the fluid, the system comprising:
    a container initially containing the cell-slurry and a supernate of the cell-slurry;
    a syringe adapted to contain the cell-slurry after dilation with the supernate;
    a fluid path between the syringe and the cell-slurry and the supernate in the container, the fluid path comprising a needle at least partially disposed in the cell-slurry and the supernate in the container and tubing fluidly connecting the needle to the syringe;
    a plunger disposed in the syringe and adapted to create pressure in the syringe to cause a dilated cell-slurry contained within the container to flow into the syringe through the fluid path;
    a fluidizing system comprising a holder adapted to move the needle to affect dilation of the cell-slurry with a portion of the supernate to form the dilated cell-slurry, the holder and the needle imparting agitating movement to the cell-slurry and the supernate in the container to affect the dilation of the cell-slurry with the supernate; and
    a control unit in communication with and adapted to control the fluidizing system and the plunger.

12. The system of claim 11, wherein the control unit comprises a processing/memory unit, a user interface adapted to allow an operator to program the control unit, and a communications interface in communications with one or more additional systems.

13. The system of claim 11, further comprising a sensor associated with the container and in electronic communication with the control unit, wherein the sensor is adapted to determine one of force of resistance to agitation, density of the cell-slurry, and amount of dilation of the cell-slurry, wherein the sensor measures one of reflection, absorbance, and transmission of light or sound.

14. The system of claim 11, wherein the container comprises a pierceable septum, and wherein the needle pierces the septum.

15. The system of claim 11, wherein the holder is a motorized holder to affect the agitating movement of the needle.

16. The system of claim 15, wherein the control unit is in communication with and adapted to control the motorized holder.

17. The system of claim 11, further comprising a stirring element within the container, wherein the stirring element is adapted to agitate the cell-slurry and the supernate in the container to affect the dilation of the cell-slurry with the supernate.

18. The system of claim 17, wherein the stirring element is moved by a motion-inducing element, and wherein the control unit is in communication with and adapted to control the motion-inducing element.

19. The system of claim 11, further comprising a motion-inducing element associated with the container to agitate the cell-slurry and the supernate to affect the dilation of the cell-slurry with the supernate by moving the container.

20. The system of claim 11, wherein the fluidizing system further comprises one or more of:
   a stirring element within the container to agitate the cell-slurry and the supernate to affect the dilation of the cell-slurry with the supernate; and
   a motion-inducing element associated with the container to agitate the cell-slurry and the supernate to affect dilation of the cell-slurry with the supernate by moving the container.

21. The system of claim 20, wherein movement of one or more of the needle, the stirring element, and the container comprises one of simple rotational motion, precessing circular motion, a precessing figure-eight motion, and combinations thereof.

22. The system of claim 11, wherein the agitating movement of the needle comprises one of simple rotational motion, precessing circular motion, a precessing figure-eight motion, and combinations thereof.

* * * * *